(12) United States Patent
Kim et al.

(10) Patent No.: US 9,373,443 B2
(45) Date of Patent: Jun. 21, 2016

(54) ELECTROMAGNETIC COIL SYSTEM FOR DRIVING CONTROL OF MICRO-ROBOT

(71) Applicant: KOREA INSTITUTE OF SCIENCE AND TECHNOLOGY, Seoul (KR)

(72) Inventors: Seung-Jong Kim, Seoul (KR); Jin Soo Kim, Seoul (KR); Jeonghoon Yoo, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 396 days.

(21) Appl. No.: 14/082,473

(22) Filed: Nov. 18, 2013

(65) Prior Publication Data

US 2014/0333143 A1     Nov. 13, 2014

(30) Foreign Application Priority Data

May 8, 2013   (KR) .................. 10-2013-0052043

(51) Int. Cl.
| | |
|---|---|
| H01F 38/14 | (2006.01) |
| H01F 7/20 | (2006.01) |
| H02J 7/16 | (2006.01) |
| A61B 1/00 | (2006.01) |

(52) U.S. Cl.
CPC ............... *H01F 38/14* (2013.01); *H01F 7/20* (2013.01); *A61B 1/00158* (2013.01); *Y10S 901/23* (2013.01)

(58) Field of Classification Search
CPC ........................................................ H02J 7/16
USPC .......................................................... 307/104
See application file for complete search history.

(56) References Cited

FOREIGN PATENT DOCUMENTS

| | | |
|---|---|---|
| JP | 2013-27271 A | 2/2013 |
| KR | 10-1003132 B1 | 12/2010 |
| KR | 10-1084722 B2 | 11/2011 |
| KR | 10-1084723 B1 | 11/2011 |

OTHER PUBLICATIONS

Korean Office Action issued Mar. 21, 2014 in counterpart Korean Patent Application No. 10-2013-0052043 (4 pages, in Korean).

*Primary Examiner* — Robert Deberadinis
(74) *Attorney, Agent, or Firm* — NSIP Law (57) ABSTRACT

An electromagnetic coil system for driving control of a micro-robot includes pairs of X-axis and Y-axis Helmholtz coils whose winding central axes are placed on an X axis and Y axis respectively, a position recognition system that detects a position and direction of the micro-robot in a workspace, a controller that controls an amount of supply of electric currents flowing to the X-axis or Y-axis Helmholtz coils in order to control movement of the micro-robot based on information about the movement of the micro-robot and previously input information about a path of the micro-robot, and a current amplifier that supplies the electric currents to the respective Helmholtz coils. The pairs of X-axis and Y-axis Helmholtz coils are disposed so as to face each other, and the X-axis Helmholtz coils and the Y-axis Helmholtz coils are vertically crossed and installed so as to form the workspace of the micro-robot.

4 Claims, 6 Drawing Sheets

ELECTROMAGNETIC COIL SYSTEM FOR DRIVING CONTROL OF MICRO-ROBOT

CROSS-REFERENCE TO RELATED APPLICATION

This application claims priority to Korean Patent Application No. 10-2013-0052043, filed on May 8, 2013, and all the benefits accruing therefrom under 35 U.S.C. §119, the contents of which in its entirety are herein incorporated by reference.

BACKGROUND

1. Field

Exemplary embodiments relate to an electromagnetic coil system for driving control of a micro-robot, and more particularly to an electromagnetic coil system that structurally requires fewer electromagnetic coils compared to an existing electromagnetic coil system for which a pair of Helmholtz coils and a pair of Maxwell coils are required, so that it can reduce a size thereof to increase space efficiency and reduce power consumption thereof to increase power efficiency.

2. Description of the Related Art

In general, existing micro-robot electromagnetic driving systems are made up of an electromagnet coil using a Helmholtz coil and a Maxwell coil, and include a power amplifier capable of applying electric current to each coil and a controller capable of measuring and controlling a position of a micro-robot.

Here, the Helmholtz coil means that a pair of same circular coils are separated from each other by a distance corresponding to a winding radius and are disposed so that winding central axes of the two coils are identical with each other. Further, the Maxwell coil means that a pair of same circular coils are separated from each other by a distance corresponding to $\sqrt{3}$ times a winding radius and are disposed so that winding central axes of the two coils are identical with each other. Meanwhile, the micro-robot refers to a small movable object of several millimeters or less in which a permanent magnet is mounted.

Figure 1:
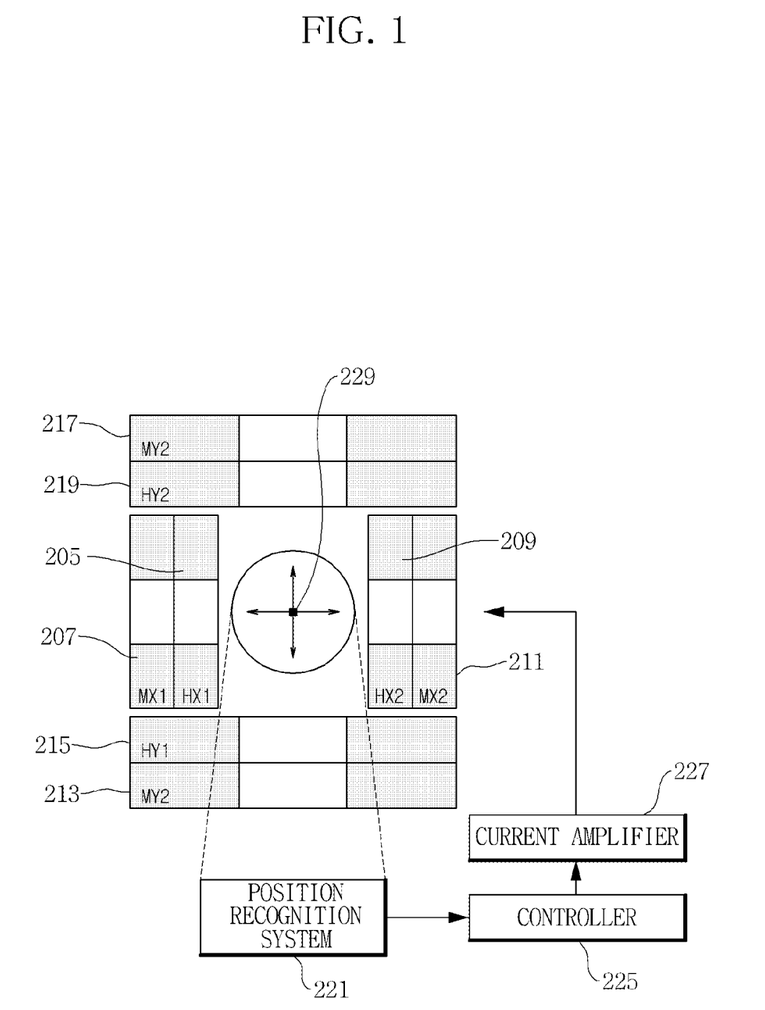
FIG. 1 is a constituent diagram showing a conventional two-dimensional electromagnetic coil system.

FIG. 1 is a constituent diagram showing a conventional two-dimensional electromagnetic coil system.

As shown in FIG. 1, a conventional electromagnetic coil system is equipped with Helmholtz coils 205, 209, 215, and 219 and Maxwell coils 207, 211, 213, and 217. The Helmholtz coils generate a uniform strength of magnetic flux within a workspace of a micro-robot 229 located in the middle between the two coils in a direction in which winding centers of the two coils are connected. The pair of Maxwell coils generates magnetic flux whose strength is increased at a constant rate in the direction. Thereby, rotation and movement of the micro-robot 229 are possible.

To be specific, first, when the uniform strength of magnetic flux is generated within the workspace of the micro-robot 229 in a winding central axis direction of the coils by applying the electric currents to the pair of Helmholtz coils 205 and 209 in the same direction, rotational torque acts on the micro-robot 229 when an internal magnetization direction of the micro-robot 229 is different from a direction of the magnetic flux (here, a horizontal direction), and the micro-robot 229 rotates in place until the magnetization direction is identical with the magnetic flux direction.

Next, when the magnetic flux constantly increased in the coil winding central axis direction is generated by applying the same electric currents to the pair of Maxwell coils 207 and 211 located in parallel outside the Helmholtz coils 205 and 209 in opposite directions, the micro-robot 229 moves in a direction in which it is aligned by the Helmholtz coils 205 and 209. In this case, a rate of change of the magnetic flux based on a distance is adjusted using an intensity of the electric currents, each of which is applied to the Maxwell coils 207 and 211. Thereby, a propulsive force applied to the micro-robot 229 can be controlled. The micro-robot 229 can be controlled so as to be propelled in the opposite direction by inverting the direction in which the electric current is applied.

This constitution is expanded. That is, as shown in FIG. 1, the Helmholtz coils 205, 209, 215, and 219 and the Maxwell coils 207, 211, 213, and 217 are disposed in pairs in X and Y axis directions orthogonal to each other. Thereby, the micro-robot can be driven on a plane (XY plane) in an arbitrary direction and to an arbitrary position.

However, since the conventional electromagnetic coil system uses a total of four pairs of coils, i.e. two pairs of Helmholtz coils and two pairs of Maxwell coils, it has a disadvantage in that it has a large volume and a lot of power consumption. Further, due to this disadvantage, above all, in the application to a medical field, due to the large volume and the lot of power consumption of the two-dimensional electromagnetic coil system for controlling driving of the micro-robot compared to the workspace of the micro-robot, there is a problem in that the practical use of the system is reduced.

SUMMARY

In accordance with an aspect of the present disclosure, there may be provided a two-dimensional electromagnetic coil system that is constructed using fewer coils than those of an existing two-dimensional electromagnetic coil system for driving control of a micro-robot, and overlaps and applies electric currents supplied to respective coils so as to be able to perform two-dimensional position control and two-dimensional direction control of the micro-robot.

In accordance with another aspect of the present disclosure, there may be provided a two-dimensional electromagnetic coil system capable of providing the same workspace and performance and reducing entire volume and power consumption, compared to an existing electromagnetic coil system.

An electromagnetic coil system for driving control of a micro-robot according to an embodiment may include a pair of X-axis Helmholtz coils whose winding central axes are placed on an X axis, a pair of Y-axis Helmholtz coils whose winding central axes are placed on a Y axis, a position recognition system that detects a position and direction of the micro-robot in a workspace, a controller that controls an amount of supply of electric currents flowing to the X-axis or Y-axis Helmholtz coils in order to control movement of the micro-robot based on information about the movement of the micro-robot obtained from the position recognition system and previously input information about a path of the micro-robot, and a current amplifier that supplies the electric currents to the respective Helmholtz coils in response to a current control instruction of the controller. The pair of X-axis Helmholtz coils are disposed so as to face each other, and the pair of Y-axis Helmholtz coils are disposed so as to face each other, and the X-axis Helmholtz coils and the Y-axis Helmholtz coils are vertically crossed and installed so as to form the workspace of the micro-robot.

Here, the controller may apply a value of the electric current, in which rotational electric currents having the same intensity and the same direction overlap with propellant electric currents having the same intensity and different directions, to the pair of X-axis Helmholtz coils or the pair of Y-axis Helmholtz coils, and performs turnabout and movement control of the micro-robot.

Further, the X-axis Helmholtz coils or the Y-axis Helmholtz coils may be cylindrical coils or quadrilateral coils.

In addition, the micro-robot may be a robot using any one of a previously magnetized permanent magnet and a magnetizable ferromagnet.

The electromagnetic coil system of the present disclosure controls a position and direction of the micro-robot only with the Helmholtz coils, so that it can simplify a complicated coil structure to reduce its volume by 50% or more, and improve capability of making efficient use of a space.

Further, the electromagnetic coil system of the present disclosure performs addition and subtraction calculation on an amount of electric current to be applied to each coil in advance, and then applies the electric current to each coil, so that it can reduce power consumption compared to a conventional electromagnetic coil system.

Further, the electromagnetic coil system of the present disclosure can be applied to a blood vessel movement robot, an intraocular robot, a digestive organ movement endoscopic robot, and so on, and thus improve technology based on a medical robot field.

DETAILED DESCRIPTION

Hereinafter, exemplary embodiments of the present disclosure will be described in further detail with reference to the accompanying drawings.

Figure 2:
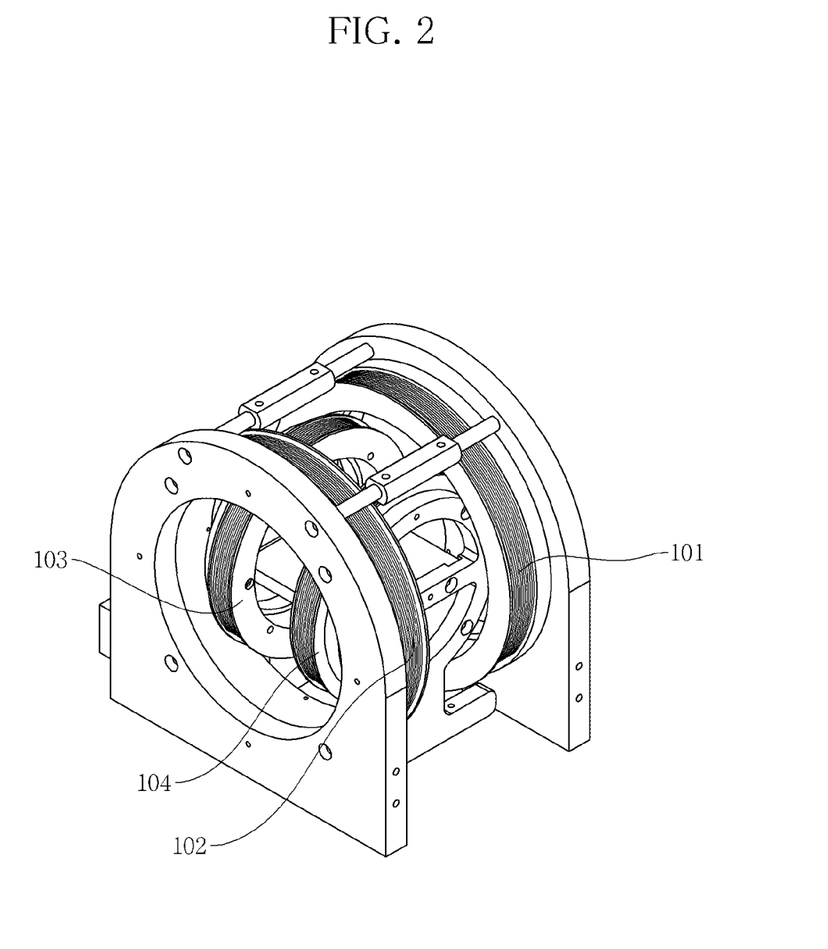
FIG. 2 is a perspective view showing an electromagnetic coil system according to an exemplary embodiment of the present disclosure.
Figure 3:
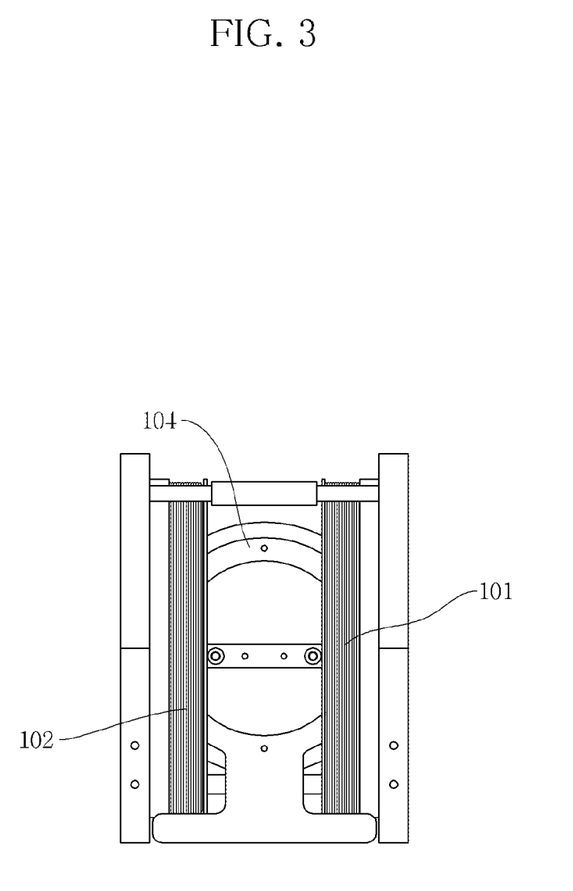
FIG. 3 is a front view of the electromagnetic coil system of FIG. 2.
Figure 4:
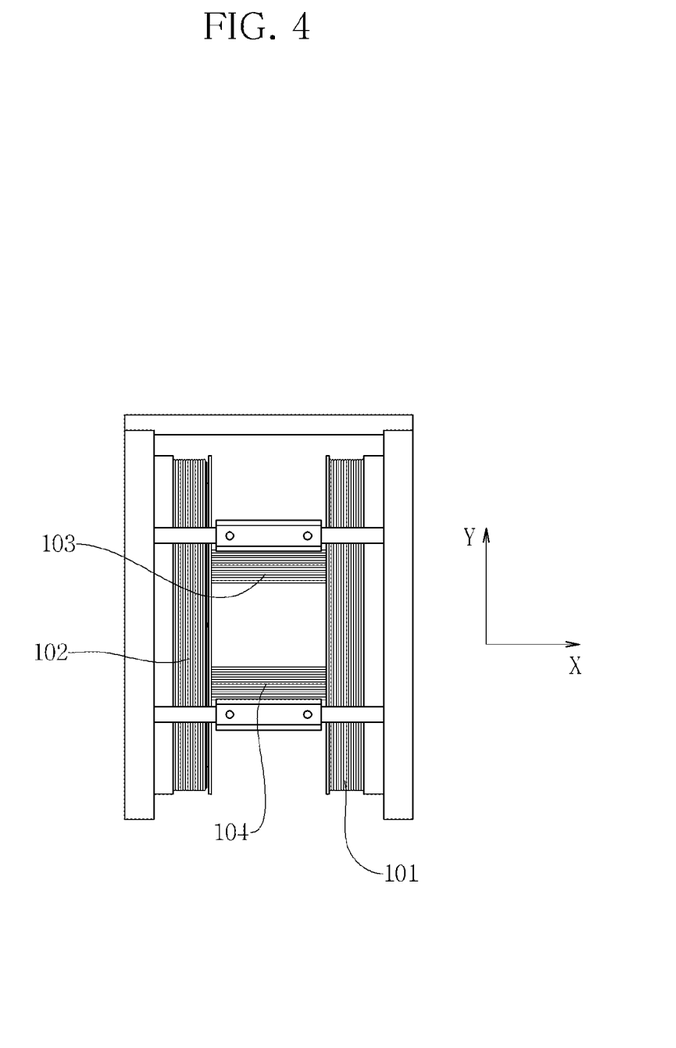
FIG. 4 is a top plan view of the electromagnetic coil system of FIG. 2.
Figure 5:
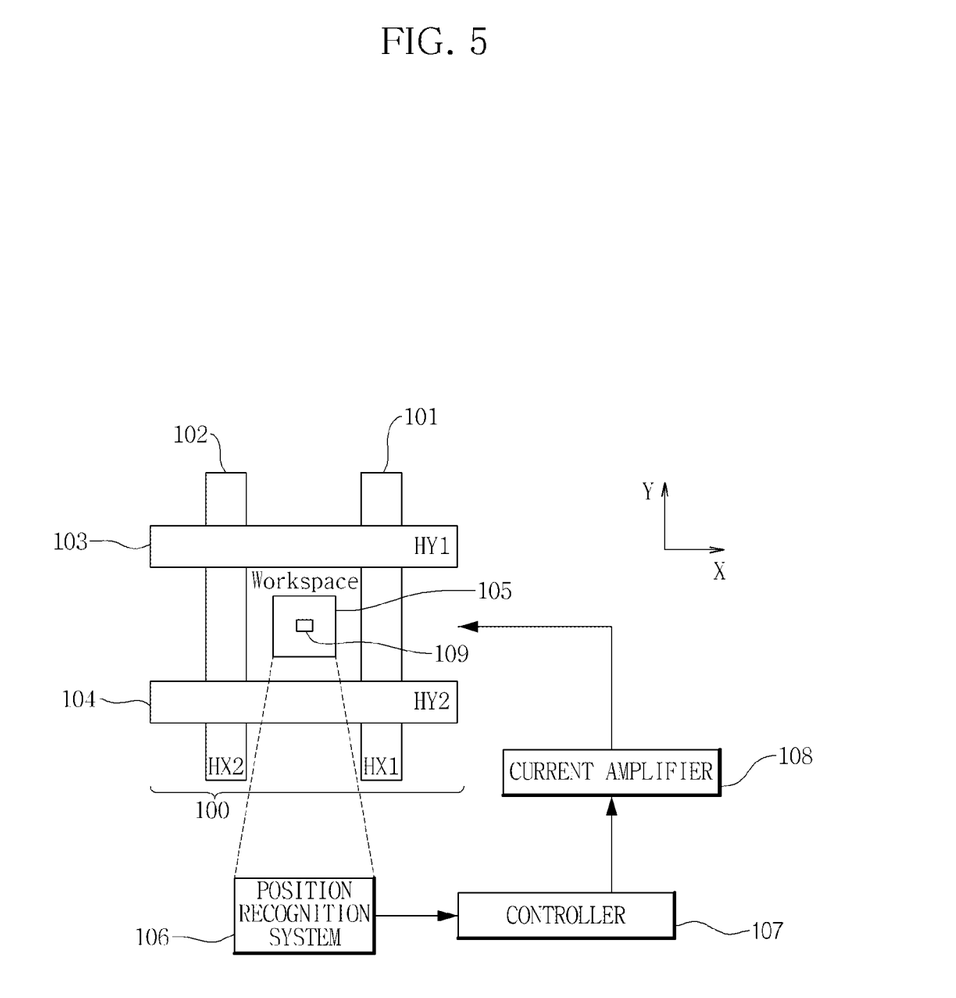
FIG. 5 is a view for describing a driving principle of the inventive electromagnetic coil system.

FIG. 2 is a perspective view showing an electromagnetic coil system according to an exemplary embodiment of the present disclosure. FIG. 3 is a front view of the electromagnetic coil system of FIG. 2. FIG. 4 is a top plan view of the electromagnetic coil system of FIG. 2. FIG. 5 is a view for describing a driving principle of the inventive electromagnetic coil system.

Referring to FIGS. 2 to 5, an electromagnetic coil system for driving control of a micro-robot 109 according to an exemplary embodiment of the present disclosure includes an electromagnetic field generating coil unit 100 installed around a workspace of the micro-robot 109, a position recognition system 106 that recognizes a position of the micro-robot 109, a controller 107 that controls electric currents so as to control turnabout and movement of the micro-robot 109 based on feedback position information, and a current amplifier 108 that supplies the electric current to each coil in response to a current control instruction of the controller 107.

The electromagnetic field generating coil unit 100 may include two pairs of Helmholtz coils 101, 102, 103, and 104 disposed in directions orthogonal to each other. The Helmholtz coils 101, 102, 103, and 104 can perform direction control as well as position control of the micro-robot 109.

Hereinafter, the direction control of the micro-robot 109 will be described first.

The direction control of the electromagnetic coil system can be performed by applying the electric currents to the pair of X-axis Helmholtz coils 101 and 102 and the pair of Y-axis Helmholtz coils 103 and 104, both of which are disposed around the workspace so as to face each other. Here, the X-axis Helmholtz coils 101 and 102 refer to coils whose winding central axes are placed on an X axis, and the Y-axis Helmholtz coils 103 and 104 refer to coils whose winding central axes are placed on a Y axis.

When the same electric currents $i_x$ are applied to the pair of X-axis Helmholtz coils 101 and 102, a magnetic field is expressed as follows.

$$B = \frac{\mu_0 n_x R_x^2 i_x}{2\left(R_x^2 + \left(\frac{R_x}{2} - x\right)^2\right)^{\frac{3}{2}}} + \frac{\mu_0 n_x R_x^2 i_x}{2\left(R_x^2 + \left(\frac{R_x}{2} + x\right)^2\right)^{\frac{3}{2}}} [T] \quad \text{Equation 1}$$

where $\mu_0$ is the magnetic permeability in a vacuum, $n_x$ is the number of winding turns of the Helmholtz coil, and $R_x$ is the winding radius of the Helmholtz coil. When the electric current having the same intensity is applied to each of the X-axis Helmholtz coils 101 and 102 in the same direction, a uniform intensity of magnetic field can be generated in the workspace in the X-axis direction. If the intensity of the magnetic field in the center of the workspace is $u_x$, $u_x$ can be expressed by the following equation.

$$B(x=0) = u_x = \left(\frac{4}{5}\right)^{1.5} \frac{\mu_0 n_x i_x}{R_x} [T] \quad \text{Equation 2}$$

Similarly, a uniform intensity of magnetic field can be generated in the Y-axis direction by applying the same electric current to each of the Y-axis Helmholtz coils 103 and 104. The uniform intensity of magnetic field can be generated on the XY plane in any direction using the two pairs of Helmholtz coils 101, 102, 103, and 104 configured in this way.

In the uniform magnetic field, a permanent magnet of the micro-robot 109 is subjected to no force, but torque so as to be aligned in a magnetic field direction. As a result, a direction of the micro-robot 109 can be aligned on the XY plane in a desired direction using the two pairs of Helmholtz coils 101, 102, 103, and 104. The torque to applied to the micro-robot 109 in the magnetic field is as follows.

$$\vec{\tau} = V\vec{M} \times \vec{B} = V\vec{M} \times (u_x \hat{x} + u_y \hat{y})[N \cdot m] \quad \text{Equation 3}$$

where V is the volume of the micro-robot 109, and $\vec{M}$ is the magnetization of the micro-robot 109. The micro-robot 109 is aligned in a direction of $$\theta = \tan^{-1}\left(\frac{u_y}{u_x}\right)$$

by the magnetic field generated by applying the electric currents having the same direction and intensity to the two pairs of Helmholtz coils 101, 102, 103, and 104.

Next, the position control of the micro-robot 109 will be described.

In an existing two-dimensional electromagnetic coil system, Maxwell coils are disposed at a distance corresponding to $\sqrt{3}$ times a winding radius, and generate magnetic flux whose strength is uniformly increased to propel a micro-robot. In the existing two-dimensional electromagnetic coil system, when the same electric currents $i_x$ are applied to the pair of Maxwell coils in the opposite directions, the magnetic field is as follows.

$$B = \frac{\mu_0 n_x R_x^2 i_x}{2\left(R_x^2 + \left(\frac{\sqrt{3}R_x}{2} - x\right)^2\right)^{\frac{3}{2}}} - \frac{\mu_0 n_x R_x^2 i_x}{2\left(R_x^2 + \left(\frac{\sqrt{3}R_x}{2} + x\right)^2\right)^{\frac{3}{2}}} [T] \quad \text{Equation 4}$$

A rate of change of the intensity of the magnetic field in the center of the workspace, which is caused by Maxwell coils, is as follows. This rate of change is called $g_x$, and $g_x$ can be expressed by the following equation.

$$\left.\frac{\partial B_x}{\partial x}\right|_{x=0} = g_x = \frac{16}{3}\left(\frac{3}{7}\right)^{2.5} \frac{\mu_0 n_x i_x}{R_x^2} [T/m] \quad \text{Equation 5}$$

In comparison with the related art as described above, the electromagnetic coil system of the present disclosure propels the micro-robot 109 using the pair of X-axis Helmholtz coils 101 and 102, and the pair of Y-axis Helmholtz coils 103 and 104 used for the direction control in order to reduce the power consumption and the volume.

When the electric currents having the same intensity are applied to the paired Helmholtz coils in the opposite directions, the magnetic flux whose strength is increased along a winding central axis can be generated. When the electric currents $i_x$ having the same intensity and different directions are applied to the X-axis Helmholtz coils 101 and 102, the magnetic field gives the effect of the conventional Maxwell coils to the Helmholtz coils 101 and 102, and thus the following equation is obtained.

$$B = \frac{\mu_0 n_x R_x^2 i_x}{2\left(R_x^2 + \left(\frac{R_x}{2} - x\right)^2\right)^{\frac{3}{2}}} - \frac{\mu_0 n_x R_x^2 i_x}{2\left(R_x^2 + \left(\frac{R_x}{2} + x\right)^2\right)^{\frac{3}{2}}} [T] \quad \text{Equation 6}$$

If a rate of change of the intensity of the magnetic field in the center of the workspace, which is caused by the Helmholtz coils 101 and 102, is expressed by $g'_x$, $g'_x$ can be expressed by the following equation.

$$\left.\frac{\partial B_x}{\partial x}\right|_{x=0} = g'_x = \frac{3}{2}\left(\frac{4}{5}\right)^{2.5} \frac{\mu_0 n_x i_x}{R_x^2} [T/m] \quad \text{Equation 7}$$

When the pair of Helmholtz coils is used, linearity can be reduced compared to the case in which the pair of Maxwell coils is used, but it is sufficient to control the micro-robot 109. Rather, a slope of the magnetic field is further increased, so that a stronger force can be produced with the same power.

Comparing Equation 5 with Equation 7, the rate of change $g'_x$ of the intensity of the magnetic field caused by the pair of Helmholtz coils 101 and 102 of the present disclosure has a value about 1.339 times greater than that $g_x$ caused by the pair of Maxwell coils of the related art. That is, a relation of $g'_x = 1.339\, g_x$ is obtained. Meanwhile, the force applied to the micro-robot 109 in the magnetic field is as follows.

$$\bar{F} = V(\bar{M}\cdot\nabla)\bar{B} = V\begin{bmatrix} M_x\frac{\partial B_x}{\partial x} + M_y\frac{\partial B_x}{\partial y} + M_z\frac{\partial B_x}{\partial z} \\ M_x\frac{\partial B_y}{\partial x} + M_y\frac{\partial B_y}{\partial y} + M_z\frac{\partial B_y}{\partial z} \\ M_x\frac{\partial B_z}{\partial x} + M_y\frac{\partial B_z}{\partial y} + M_z\frac{\partial B_z}{\partial z} \end{bmatrix} [N\cdot m] \quad \text{Equation 8}$$

When the electric currents having the same intensity are applied to the pair of Helmholtz coils 101 and 102, and the pair of Helmholtz coils 103 and 104 in the opposite directions, the force applied to the micro-robot 109 is as follows.

$$\begin{bmatrix} F_x \\ F_y \end{bmatrix} = VM\begin{bmatrix} \cos\theta(g'_x - 0.5g'_y) \\ \sin\theta(g'_y - 0.5g'_x) \end{bmatrix}[N\cdot m] \quad \text{Equation 9}$$

where V is the volume of the micro-robot 109, and M is the magnetization of the micro-robot 109. In the conventional electromagnetic coil system shown in FIG. 1, the slope of the magnetic flux generated by the pair of X-axis Maxwell coils 207 and 211 and the slope of the magnetic flux generated by the pair of Y-axis Maxwell coils 213 and 217 are caused to be identical to each other ($g_x = g_y$), and the micro-robot 229 is propelled in the aligned direction ($\theta$). That is, the force applied to the micro-robot 229 in the existing two-dimensional electromagnetic coil system is as follows.

$$F_x = 0.5 g_x \times VM \cos\theta \cdot F_y = 0.5 g_y \times VM \sin\theta \quad \text{Equation 10}$$

In comparison with the conventional electromagnetic coil system, the electromagnetic coil system of the present disclosure can consume less power while applying the same force. To this end, the electric currents are applied so that the slope of the magnetic flux generated by the pair of X-axis Helmholtz coils 101 and 102 and the slope of the magnetic flux generated by the pair of Y-axis Helmholtz coils 103 and 104 have the same value and different signs, i.e. opposite signs ($g'_x = -g'_y$). When the electric currents are applied in this way, the force applied to the micro-robot 109 is as follows.

$$F'_x = 1.5 g'_x \times VM\cos\theta,\ F'_y = -1.5 g'_x \times VM\sin\theta \quad \text{Equation 11}$$

$$\frac{F'_y}{F'_x} = -\tan\theta = \tan(2\pi - \theta)$$

That is, the micro-robot 109 aligned in the $\theta$ direction can be propelled in a direction of $\dot\theta = 2\pi - \theta$. The fact that the direction in which the micro-robot 109 is propelled is different from the magnetization vector $\vec{M}$ of the micro-robot 109 becomes no issue in controlling the movement of the micro-robot 109. Rather, since this control technique is selected, the force of about 4 times the existing force that can be exerted can be produced although the same electric currents are applied. That is, comparing $F_x$ and $F_y$ of Equation 10 with $F'_x$ and $F'_y$ of Equation 11, since $g'_x = 1.339\, g_x$, when the same electric currents are applied, $F'_x$ and $F'_y$ can be produced by about 4 times compared to $F_x$ and $F_y$.

In addition to this, as described above, the electric currents required to rotate the micro-robot 109 overlap with those required to propel the micro-robot 109. Thereby, the directions of the electric currents flowing to the Helmholtz coils and the Maxwell coils in the conventional electromagnetic coil system are opposite to each other, so that offset components can be removed and thus consumed power can be reduced.

Referring to FIG. 5 again, the position recognition system 106 detects the position and direction of the micro-robot 109 in the workspace. The position recognition system 106 may use a camera when driven in an environment that is exposed to the outside, and computed tomography (CT) or magnetic resonance imaging (MRI) when driven in an environment that is not exposed to the outside.

Information about the position and direction of the micro-robot 109 detected by the position recognition system 106 is input to the controller 107. The controller 107 controls an amount of supply of the electric currents flowing to the Helmholtz coils 101, 102, 103, and 104 in order to control the movement of the micro-robot 109 based on the information about the movement of the micro-robot 109 obtained from the position recognition system 106 and the previously input information about a path of the micro-robot 109.

The current amplifier 108 supplies the electric current to each of the Helmholtz coils 101, 102, 103, and 104 in response to a current control instruction of the controller 107.

Figure 6:
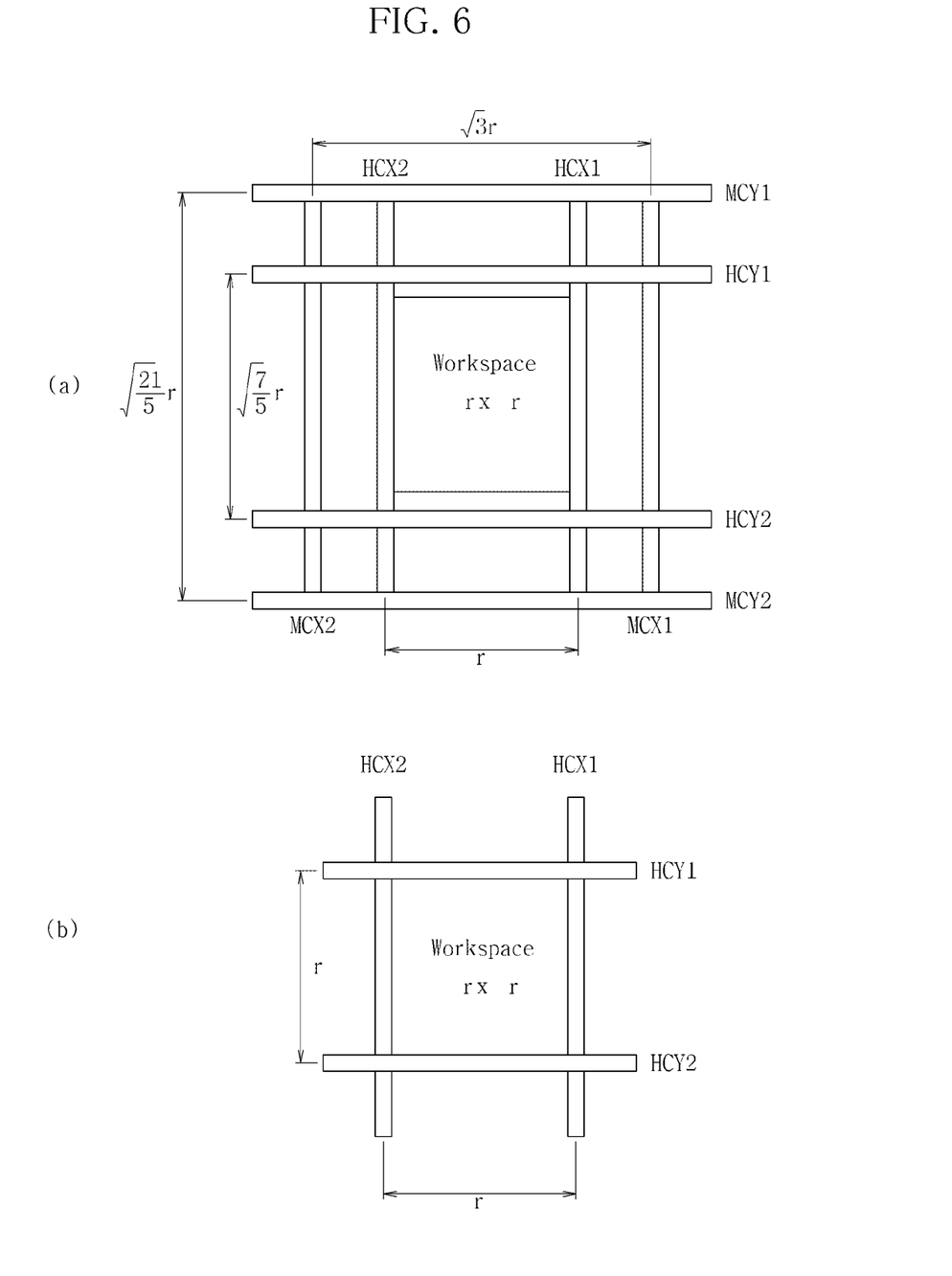
FIG. 6 is a view for comparing a conventional electromagnetic coil system with the electromagnetic coil system of the present disclosure.

FIG. 6 is a view for comparing a conventional electromagnetic coil system and the electromagnetic coil system of the present disclosure. FIG. 6(a) is a top plan view showing a structure of the conventional electromagnetic coil system, and FIG. 6(b) is a top plan view showing a structure of the electromagnetic coil system of the present disclosure.

As shown in FIG. 6, the electromagnetic coil system of the present disclosure has a shape in which a volume thereof is reduced compared to the conventional electromagnetic coil system, and can produce a stronger force when the same electric currents are applied as described above.

The electromagnetic coil system of the present disclosure can perform rotation control as well as movement control of the micro-robot 109 using only the paired Helmholtz coils 101, 102, 103, and 104 without the Maxwell coils. To this end, the same electric currents are not applied to the paired Helmholtz coils 101 and 102 or the paired Helmholtz coils 103 and 104, but different electric currents are applied to the paired Helmholtz coils 101 and 102 or the paired Helmholtz coils 103 and 104 so that the magnetic field similar to that generated in the workspace of the micro-robot by the Helmholtz coils and the Maxwell coils in the related art. When the concept of the present disclosure is expanded, three-degree-of-freedom movement control of the micro-robot 109 can be performed by applying three pairs of Helmholtz coils.

Although the present disclosure has been described with reference to the embodiments shown in the drawings, these embodiments are illustrative only and those skilled in the art will appreciate that various modifications, additions and substitutions are possible, without departing from the technical protection scope of the present invention. Therefore, the true technical protection scope of the present disclosure should be defined by the technical spirit of the appended claims.

What is claimed is:

1. An electromagnetic coil system for driving control of a micro-robot comprising:
    a pair of X-axis Helmholtz coils whose winding central axes are placed on an X axis;
    a pair of Y-axis Helmholtz coils whose winding central axes are placed on a Y axis;
    a position recognition system that detects a position and direction of the micro-robot in a workspace;
    a controller that controls an amount of supply of electric currents flowing to the X-axis or Y-axis Helmholtz coils in order to control movement of the micro-robot based on information about the movement of the micro-robot obtained from the position recognition system and previously input information about a path of the micro-robot; and
    a current amplifier that supplies the electric currents to the respective Helmholtz coils in response to a current control instruction of the controller,
    wherein the pair of X-axis Helmholtz coils are disposed so as to face each other, and the pair of Y-axis Helmholtz coils are disposed so as to face each other, and the X-axis Helmholtz coils and the Y-axis Helmholtz coils are vertically crossed and installed so as to form the workspace of the micro-robot.

2. The electromagnetic coil system of claim 1, wherein the controller applies a value of the electric current, in which rotational electric currents having the same intensity and the same direction overlap with propellant electric currents having the same intensity and different directions, to the pair of X-axis Helmholtz coils or the pair of Y-axis Helmholtz coils, and performs turnabout and movement control of the micro-robot.

3. The electromagnetic coil system of claim 1, wherein the X-axis Helmholtz coils or the Y-axis Helmholtz coils are cylindrical coils or quadrilateral coils.

4. The electromagnetic coil system of claim 1, wherein the micro-robot is a robot using any one of a previously magnetized permanent magnet and a magnetizable ferromagnet.

* * * * *